(12) United States Patent
Fraser et al.

(10) Patent No.: US 8,591,588 B2
(45) Date of Patent: Nov. 26, 2013

(54) SPINAL FIXATION PLATE

(75) Inventors: Robert D. Fraser, Myrtle Bank (AU); John D. Malone, Franklin, MA (US); Hassan A. Serhan, South Easton, MA (US); Richard C. Techiera, New Bedford, MA (US)

(73) Assignee: DePuy Synthes Products, LLC, Raynham, MA (US)

( * ) Notice: Subject to any disclaimer, the term of this patent is extended or adjusted under 35 U.S.C. 154(b) by 312 days.

(21) Appl. No.: 12/883,832

(22) Filed: Sep. 16, 2010

(65) Prior Publication Data

US 2011/0004253 A1    Jan. 6, 2011

Related U.S. Application Data

(60) Division of application No. 10/927,778, filed on Aug. 27, 2004, now Pat. No. 7,819,903, which is a continuation-in-part of application No. 10/403,930, filed on Mar. 31, 2003, now Pat. No. 7,112,222.

(51) Int. Cl.
*A61F 2/44* (2006.01)
*A61B 17/80* (2006.01)

(52) U.S. Cl.
USPC .................. 623/17.16; 606/286; 606/297

(58) Field of Classification Search
USPC ......... 606/70, 71, 280–299; 623/17.11–17.16
See application file for complete search history.

(56) References Cited

U.S. PATENT DOCUMENTS

| | | |
|---|---|---|
| 4,599,086 A | 7/1986 | Doty |
| 4,743,256 A | 5/1988 | Brantigan |
| 4,834,757 A | 5/1989 | Brantigan |
| 4,878,915 A | 11/1989 | Brantigan |
| 5,180,381 A | 1/1993 | Aust et al. |
| 5,192,327 A | 3/1993 | Brantigan |
| 5,306,309 A | 4/1994 | Wagner et al. |
| 5,397,364 A | 3/1995 | Kozak et al. |
| 5,405,391 A * | 4/1995 | Hednerson et al. ........ 623/17.15 |
| 5,425,772 A | 6/1995 | Brantigan |
| 5,443,515 A | 8/1995 | Cohen et al. |
| 5,522,899 A | 6/1996 | Michelson |
| 5,549,612 A | 8/1996 | Yapp et al. |

(Continued)

FOREIGN PATENT DOCUMENTS

DE    29511146 U1    11/1995
FR    2742653 A1    6/1997

(Continued)

*Primary Examiner* — Matthew Lawson
(74) *Attorney, Agent, or Firm* — Nutter McClennen & Fish LLP

(57) ABSTRACT

Spinal fixation plates for maintaining adjacent vertebrae in and fixed position are provided. In an exemplary embodiment, the plate includes opposed superior and inferior portions that are angled in a direction anterior to an anterior face of a mid-portion of the plate. The plate also includes a curvature formed therein about a longitudinal axis in a sagittal plane thereof. In use, when the plate is attached to adjacent vertebrae, the angle of the superior and inferior portions and the curvature in the plate are effective to position one or more thru-bores formed in the superior and inferior portions at the anterior rims of the adjacent vertebrae. In another embodiment, a spinal fixation plate is provided that is adapted to engage and mate to a fusion cage or other vertebral implant disposed between adjacent vertebra. The present invention also provides spinal fixation kits or assemblies, and methods for implanting the same.

16 Claims, 10 Drawing Sheets

(56) References Cited

U.S. PATENT DOCUMENTS

| | | | |
|---|---|---|---|
| 5,607,424 A | 3/1997 | Tropiano |
| 5,658,335 A | 8/1997 | Allen |
| 5,658,337 A | 8/1997 | Kohrs et al. |
| 5,713,899 A | 2/1998 | Marnay et al. |
| 5,716,415 A | 2/1998 | Steffee |
| 5,755,798 A | 5/1998 | Papavero et al. |
| 5,766,252 A | 6/1998 | Henry et al. |
| 5,776,199 A | 7/1998 | Michelson |
| 5,782,832 A | 7/1998 | Larsen et al. |
| 5,800,550 A | 9/1998 | Sertich |
| 5,824,094 A | 10/1998 | Serhan et al. |
| 5,861,041 A | 1/1999 | Tienboon |
| 5,865,845 A | 2/1999 | Thalgott |
| 5,888,227 A | 3/1999 | Cottle |
| 5,888,228 A | 3/1999 | Knothe et al. |
| 5,904,683 A | 5/1999 | Pohndorf et al. |
| 5,954,722 A | 9/1999 | Bono |
| 5,961,554 A | 10/1999 | Janson et al. |
| 5,964,807 A | 10/1999 | Gan et al. |
| 5,976,187 A | 11/1999 | Richelsoph |
| 6,019,793 A | 2/2000 | Perren et al. |
| 6,045,579 A | 4/2000 | Hochshuler et al. |
| 6,080,193 A | 6/2000 | Hochshuler et al. |
| 6,093,205 A | 7/2000 | McLeod et al. |
| 6,096,080 A | 8/2000 | Nicholson et al. |
| 6,113,638 A | 9/2000 | Williams et al. |
| 6,120,503 A | 9/2000 | Michelson |
| 6,156,037 A | 12/2000 | LeHuec et al. |
| 6,168,596 B1 | 1/2001 | Wellisz et al. |
| 6,176,882 B1 | 1/2001 | Biedermann et al. |
| 6,224,602 B1 | 5/2001 | Hayes |
| 6,231,610 B1 | 5/2001 | Geisler |
| 6,235,033 B1 | 5/2001 | Brace et al. |
| 6,235,059 B1 | 5/2001 | Benezech et al. |
| 6,290,703 B1 | 9/2001 | Ganem |
| 6,306,170 B2 | 10/2001 | Ray |
| 6,342,055 B1 * | 1/2002 | Eisermann et al. | 623/17.16 |
| 6,428,542 B1 | 8/2002 | Michelson |
| 6,432,106 B1 * | 8/2002 | Fraser | 623/17.11 |
| 6,565,571 B1 | 5/2003 | Jackowski et al. |
| 6,576,017 B2 * | 6/2003 | Foley et al. | 623/17.16 |
| 6,585,769 B1 | 7/2003 | Muhanna et al. |
| 6,602,256 B1 | 8/2003 | Hayes |
| 6,613,091 B1 | 9/2003 | Zdeblick et al. |
| 6,712,820 B2 | 3/2004 | Orbay |
| 6,740,088 B1 | 5/2004 | Kozak |
| 6,835,206 B2 | 12/2004 | Jackson |
| 6,892,586 B1 | 5/2005 | Welch et al. |
| 6,916,320 B2 | 7/2005 | Michelson |
| 7,077,843 B2 | 7/2006 | Thramann et al. |
| 7,112,222 B2 | 9/2006 | Fraser et al. |
| 7,273,481 B2 | 9/2007 | Lombardo et al. |
| 7,276,070 B2 | 10/2007 | Muckter |
| 7,306,605 B2 | 12/2007 | Ross |
| 7,481,829 B2 | 1/2009 | Baynham et al. |
| 7,608,096 B2 | 10/2009 | Foley et al. |
| 7,819,903 B2 | 10/2010 | Fraser et al. |
| 7,833,245 B2 * | 11/2010 | Kaes et al. | 606/246 |
| 2003/0125739 A1 * | 7/2003 | Bagga et al. | 606/61 |
| 2003/0187443 A1 | 10/2003 | Lauryssen et al. |
| 2004/0193269 A1 | 9/2004 | Fraser et al. |
| 2004/0199254 A1 | 10/2004 | Louis et al. |
| 2004/0220571 A1 | 11/2004 | Assaker et al. |
| 2005/0033294 A1 * | 2/2005 | Garden et al. | 606/61 |
| 2005/0085913 A1 | 4/2005 | Fraser et al. |
| 2005/0216081 A1 * | 9/2005 | Taylor | 623/17.11 |
| 2005/0228382 A1 | 10/2005 | Richelsoph et al. |

FOREIGN PATENT DOCUMENTS

| | | |
|---|---|---|
| FR | 2747034 A1 | 10/1997 |
| WO | WO-9720526 A1 | 6/1997 |
| WO | WO-9963914 A1 | 12/1999 |

\* cited by examiner

SPINAL FIXATION PLATE

CROSS-REFERENCE TO RELATED APPLICATIONS

This application is a divisional of U.S. patent application Ser. No. 10/927,778, filed on Aug. 27, 2004 and entitled "Spinal Fixation Plates," which is a continuation-in-part of U.S. patent application Ser. No. 10/403,930 (now U.S. Pat. No. 7,112,222), filed on Mar. 31, 2003 and entitled "Anterior Lumbar Interbody Fusion Cage With Locking Plate." These references are hereby expressly incorporated herein by reference.

FIELD OF THE INVENTION

The present invention relates to medical devices, and more particularly to spinal fixation plates for promoting fusion of adjacent vertebral bodies.

BACKGROUND OF THE INVENTION

Advancing age, as well as injury, can lead to changes in the bones, disks, joints, and ligaments of the spine producing pain from nerve root compression. Under certain circumstances, alleviation of pain can be provided by performing a spinal fusion. This is a procedure that involves joining two or more adjacent vertebrae with a bone fixation device so that they no longer are able to move relative to each other. For a number of known reasons, bone fixation devices are useful for promoting proper healing of injured or damaged vertebral bone segments caused by trauma, tumor growth, or degenerative disc disease. The external fixation devices immobilize the injured bone segments to ensure the proper growth of new osseous tissue between the damaged segments. These types of external bone fixation devices often include internal bracing and instrumentation to stabilize the spinal column to facilitate the efficient healing of the damaged area without deformity or instability, while minimizing any immobilization and post-operative care of the patient.

One such device is a bone fixation plate that is used to immobilize adjacent skeletal parts such as bones. Typically, the fixation plate is a rigid metal or polymeric plate positioned to span bones or bone segments that require immobilization with respect to one another. The plate is fastened to the respective bones, usually with bone screws, so that the plate remains in contact with the bones and fixes them in a desired position. Bone plates can be useful in providing the mechanical support necessary to keep vertebral bodies in proper position and bridge a weakened or diseased area such as when a disc, vertebral body or fragment has been removed.

Such plates have been used to immobilize a variety of bones, including vertebral bodies of the spine. These bone plate systems usually include a rigid bone plate having a plurality of screw openings. The openings are either holes or slots to allow for freedom of screw movement. The bone plate is placed against the damaged vertebral bodies and bone screws are used to secure the bone plate to the spine and optionally to a prosthetic implant positioned between the adjacent vertebrae.

While several types of bone fixation plates exists, there remains a need for improved spinal fixation plates.

SUMMARY OF THE INVENTION

The present invention generally provides spinal fixation plates, spinal implants for use with spinal fixation plates, and methods for implanting the same. In one embodiment of the present invention, a spinal fixation plate is provided for maintaining adjacent vertebrae in a fixed position with respect to one another. The fixation plate includes a mid-portion with opposed superior and inferior portions. The superior and inferior portions can each include at least one thru-bore formed therein for receiving a fastening element, and the superior and inferior portions are preferably positioned at an angle with respect to the mid-portion such that, when the plate is positioned in relation to adjacent superior and inferior vertebrae, the superior and inferior portions of the plate are positioned adjacent to the anterior rim of each vertebra. In an exemplary embodiment, the superior and inferior portions are angled in a direction anterior to the anterior face of the mid-portion, and the angle is preferably less than about 15°.

In one exemplary embodiment, the plate can include a posterior curvature formed about a longitudinal axis. As a result, the plate can have a substantially concave posterior face, and the plate can also optionally have a substantially convex anterior face. In another embodiment, the superior and inferior portions of the plate preferably each include first and second thru-bore tabs formed on opposed sides of the longitudinal axis of the plate. When combined with the curvature in the plate, the first and second opposed tabs can be angled toward one another in a posterior direction. In an exemplary embodiment, the angle between a posterior face of the first thru-bore tab and a posterior face of the second thru-bore tab in each of the superior and inferior portions is in the range of about 150° to 180°, and more preferably the angle is about 160°.

In yet another embodiment of the present invention, a spinal fixation plate is provided having a mid-portion and opposed superior and inferior portions extending at an angle with respect to the mid-portion in a direction anterior to an anterior face of the mid-portion. The superior and inferior portions each preferably include first and second thru-bore tabs formed on opposed sides of a longitudinal axis of the plate. The first and second thru-bores tabs are preferably angled toward one another in a posterior direction. The first and second thru-bores tabs in the superior and inferior portions also preferably each include a thru-bore formed therein and adapted to receive a fastening element to mate the plate to adjacent vertebrae. The mid-portion can also optionally be curved about a longitudinal axis, preferably in a posterior direction, such that opposed side edges of the mid-portion are positioned posterior to a posterior face of the mid-portion at the longitudinal axis of the mid-portion. At least a portion of the plate can have a substantially concave posterior face as a result of the curve formed therein. At least a portion of the plate can also optionally have a substantially convex anterior face as a result of the curve formed therein.

The present invention also provides a spinal fixation kit that includes at least one fixation plate and an implant that is adapted to be disposed between adjacent vertebra and that has posterior, anterior, superior, and inferior faces. The fixation plate preferably has a mid-portion with opposed superior and inferior portions that define a plate length that is preferably greater than a height of the implant between the superior and inferior faces. The superior and inferior portions also preferably include first and second opposed thru-bore tabs that extend in a direction anterior to an anterior face of the mid-portion of the fixation plate, and/or that extend at an angle toward one another in a posterior direction. The kit can also include at least one fastening element that is adapted to extend through a thru-bore tab in the superior and inferior portions of the fixation plate to mate the plate to adjacent vertebrae.

The present invention also provides methods for implanting a spinal fixation plate. In one exemplary embodiment, the method can include one or more of the following steps: distracting adjacent vertebrae, removing at least a portion of the disc disposed between the adjacent vertebrae, positioning a spinal implant between the adjacent vertebrae, and positioning a spinal fixation plate adjacent to an anterior face of the spinal implant such the opposed superior and inferior portions of the spinal fixation plate are positioned on the anterior rim of each vertebra. A fastening element can then be inserted through one or more of the thru-bore formed in the spinal fixation plate to attach the spinal fixation plate to the adjacent vertebrae. In an exemplary embodiment, the superior and inferior portions of the spinal fixation plate include longitudinally opposed thru-bores tabs, each having a thru-bore formed therein for receiving a fastening element. The opposed thru-bore tabs in the superior portion are preferably angled toward one another in a posterior direction, and the thru-bore tabs in the inferior portion are also preferably angled toward one another in a posterior direction. The superior and inferior portions of the plate can also be angled in a direction anterior to an anterior face of a mid-portion of the plate, such that the mid-portion of the plate is flush or sub-flush relative to an anterior face of the adjacent vertebrae.

In yet another embodiment of the present invention, a spinal fixation assembly is provided including a fusion cage with posterior, anterior, superior, and inferior faces, and a plate having at least one aperture for receiving a bone screw and being configuration to slidably mate to the fusion cage. In one embodiment, the plate includes a mating element for engaging the cage in an anterior-posterior direction. The mating element can have a variety of configurations, but it preferably takes the form of opposed first and second arms that are adapted to engage the superior and inferior faces of the fusion cage. The first and second arms can be flexible, and preferably extend from the plate and are adapted to seat on the superior and inferior faces of the fusion cage. The superior and inferior faces of the fusion cage can each include an arm-seating recess formed therein for receiving the first and second arms on the plate. These recesses allow the arms to sit flush with the superior and inferior faces when disposed within the arm-seating recesses. In an exemplary embodiment, the first and second arms are adapted to mate with the arm-receiving recesses formed on the fusion cage with an interference fit to temporarily secure the plate to the fusion cage.

In another embodiment, the anterior face of the fusion cage can include at least one bore formed therein, and the mating element can be at least one arm that is adapted to extend into the bore in the fusion cage to mate the plate to the fusion cage. In a preferred embodiment, the anterior face of the fusion cage includes a superior bore and an inferior bore formed therein, and the mating element comprises opposed first and second arms that are adapted to extend into the superior and inferior bores in the fusion cage to mate the plate to the fusion cage.

In another embodiment, the fusion cage includes an intermediate plane that separates the inferior face from the superior face to define an inferior side and a superior side, and the plate includes at least one inferior aperture on the inferior side of the fusion cage and at least one superior aperture on the superior side of the fusion cage. Each aperture in the plate can have a first end having an opening, a second, opposed end, and a sidewall extending therebetween that defines an inner lumen. The first end of each aperture preferably is a generally spherical recess formed in the plate for rotatably seating a head of a bone screw. A split bushing is preferably disposed within each aperture in the plate. Each aperture can optionally include an anti-rotation mechanism effective to prevent each split bushing from rotating within the aperture. The apertures and the split bushings can have a variety of configurations. In one embodiment, the sidewall of each aperture can be concave and each split bushing can include a convex outer surface. Each split bushing can also optionally include a shoulder formed therein that abuts a corresponding shoulder formed within each aperture. In another embodiment, each split bushing can include an inner surface having threads formed thereon that are adapted to mate with corresponding threads formed on a bone screw.

In other aspects, the inferior and superior apertures are disposed in inferior and superior portions. The portions, or tabs, are preferably angled with respect to the fusion cage in a direction anterior to the anterior face of the fusion cage. In an exemplary embodiment, each portion extends in a plane, and each aperture defines a central axis that extends through the aperture at an angle with respect to the plane of the portion in which the aperture is disposed.

BRIEF DESCRIPTION OF THE DRAWINGS

The invention will be more fully understood from the following detailed description taken in conjunction with the accompanying drawings, in which.

DETAILED DESCRIPTION OF THE DRAWINGS

Figure 1A:
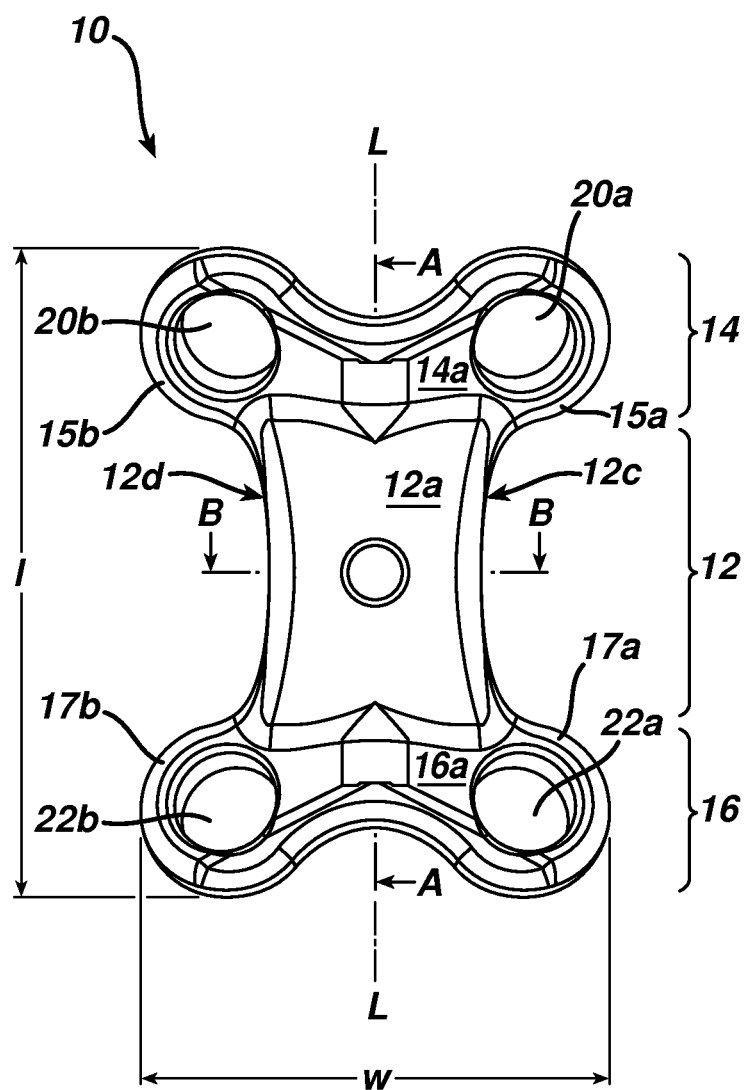
FIG. 1A illustrates an anterior view of one embodiment of a spinal fixation plate in accordance with the present invention.

In general, the present invention provides a spinal fixation plate having at least one aperture for receiving a bone screw. The plate is adapted to be attached to adjacent vertebrae to maintain the vertebrae in and fixed position and thereby provide biomechanical stability to the vertebra. The plate can be used in connection with a variety of spinal implants, including inner body fusion devices, fusion cages, bone grafts, artificial discs, or other vertebral implants, and it can optionally be adapted for use in both mating or non-mating relationships with the inner body fusion devices or other vertebral implant.

FIGS. 1A-2B illustrate one embodiment of spinal fixation plate 10. In general, the plate 10 has a substantially elongate shape and it includes a mid-portion 12 that is positioned between superior and inferior portions 14, 16. Each portion 12, 14, 16 includes an anterior face 12a, 14a, 16a and a posterior face 12b, 14b, 16b, respectively, and the portions 12, 14, 16 together define a longitudinal axis L extending therealong. The mid-portion 12 of the plate 10 also includes opposed lateral sides 12c, 12d extending therealong between the superior and inferior portions 14, 16.

As indicated above, the superior and inferior portions 14, 16 are adapted to mate to superior and inferior vertebrae, respectively, and the mid-portion 12 extends therebetween to maintain the vertebrae at a fixed position with respect to one another. Accordingly, the plate 10 preferably includes one or more apertures or thru-bores formed therein for receiving a fastening element, such as a bone screw, to attach the plate 10 to the adjacent vertebrae. In the illustrated exemplary embodiment, each portion 14, 16 includes two thru-bores 20a, 20b, 22a, 22b formed therein. The thru-bores 20a, 20b, 22a, 22b are preferably formed on opposed sides of the longitudinal axis L of the plate 10 such that each of the superior and inferior portions 14, 16 of the plate 10 include first and second opposed thru-bore tabs 15a, 15b, 17a, 17b. The thru-bores 20a, 20b, 22a, 22b can have a variety of configurations, and exemplary configurations will be discussed in more detail with respect to FIGS. 6-10.

Figure 2A:
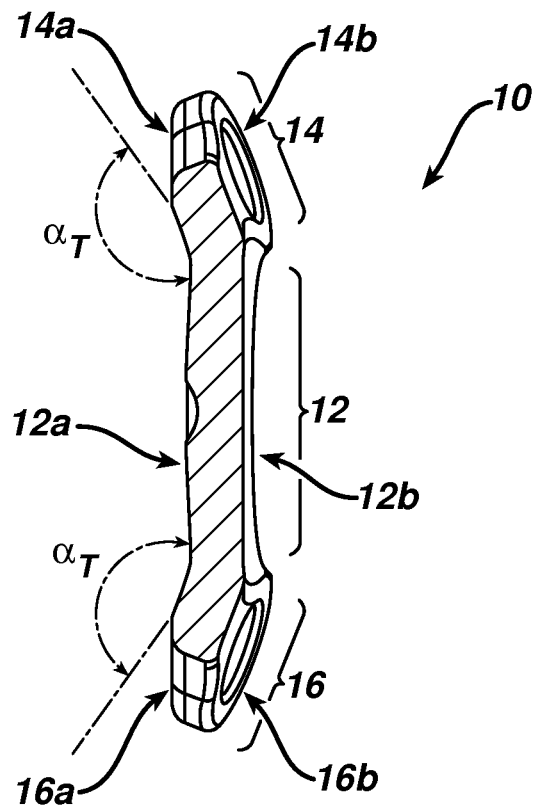
FIG. 2A is a cross-sectional view of the fixation plate shown in FIG. 1A taken along line A-A.

The superior and inferior portions 14, 16 of the plate 10 can also be adapted to position the thru-bores 20a, 20b, 22a, 22b at a particular location with respect to the adjacent vertebrae. In an exemplary embodiment, the superior and inferior portions 14, 16 can be angled with respect to the mid-portion 12 and more particularly, as best shown in FIG. 2A, the superior and inferior portions 14, 16 can extend in a direction that is anterior to the anterior face 12a of the mid-portion 12. As a result, when the plate 10 is implanted, the superior and inferior portions 14, 16 can be positioned on the anterior rim of each vertebra, which is a location that is between the anterior face and the endplate of each vertebra, e.g., along an edge of the vertebrae at the endplate/cortical junction. This location, which will be discussed in more detail with respect to FIG. 2C, is hereinafter referred to as the anterior rim of a vertebra. When the superior and inferior portions 14, 16 are positioned against the anterior rims, the angle α also causes the mid-portion 12 to be substantially flush or sub-flush with respect to the anterior surface of each vertebra, thereby minimizing the anterior prominence of the plate 10. The position also allows locking mechanisms, such as bone screws, to be inserted through the thru-bores 20a, 20b, 22a, 22b, through the anterior rims of the vertebrae, and into the vertebral bodies. The unique positioning of the plate 10 also reduces the need for excessive vessel retraction.

The angulation of the superior and inferior portions 14, 16 can vary depending on the intended use, but in an exemplary embodiment the angle $\alpha_T$ between the anterior surface 14a, 16a of the superior and inferior portions 14, 16 and the anterior surface 12a of the mid-portion 12 is less than about 15°, and more preferably the angle $\alpha_T$ is about 10°. A person having ordinary skill in the art will appreciate that the angle $\alpha_T$ can be greater than 15°.

Figure 1B:
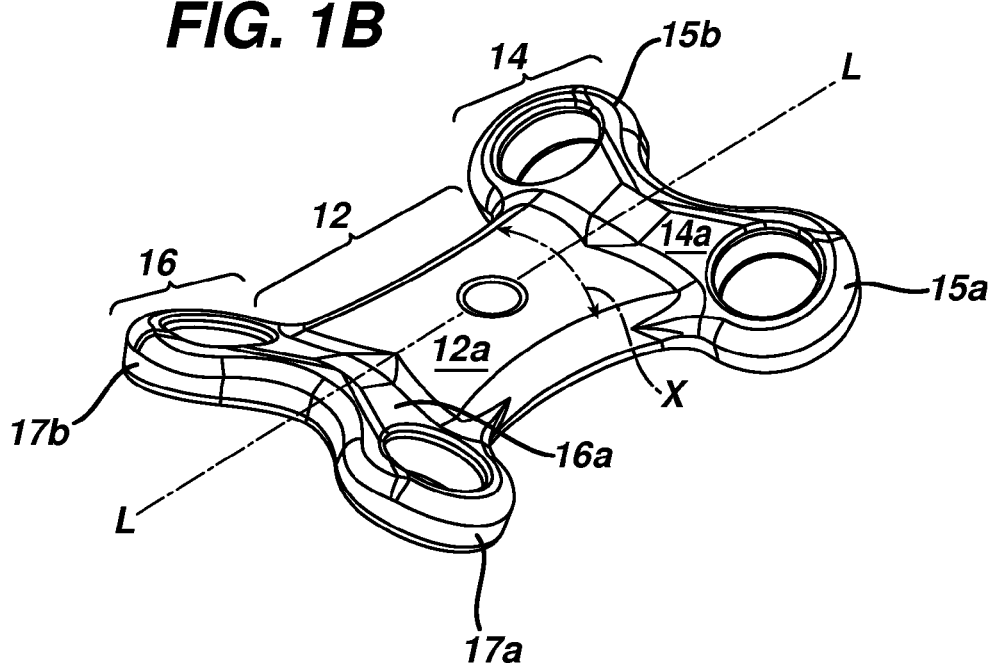
FIG. 1B is an anterior perspective view of the fixation plate shown in FIG. 1A.
Figure 1C:
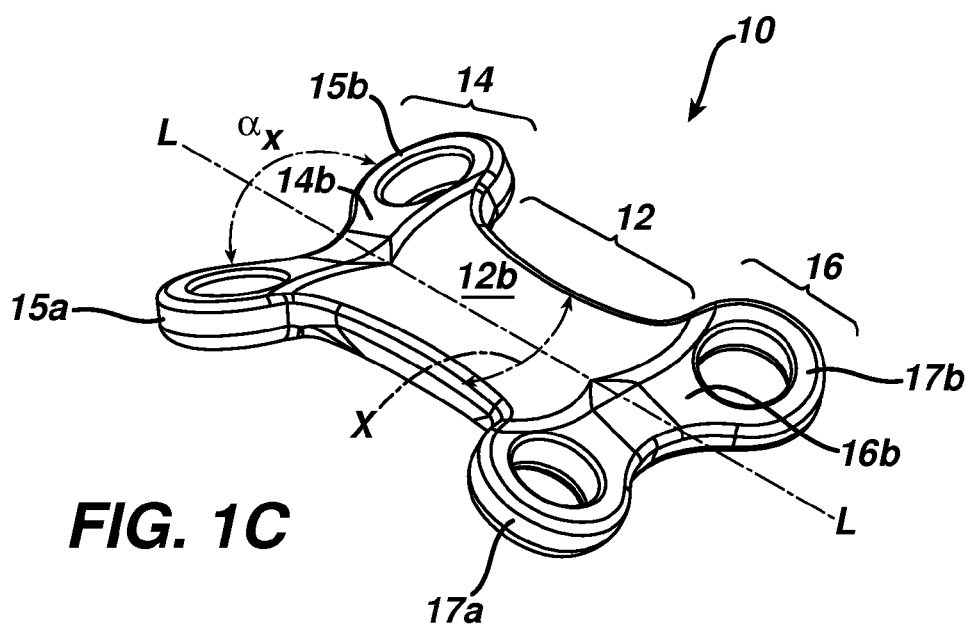
FIG. 1C is a posterior perspective view of the fixation plate shown in FIG. 1A.
Figure 2B:
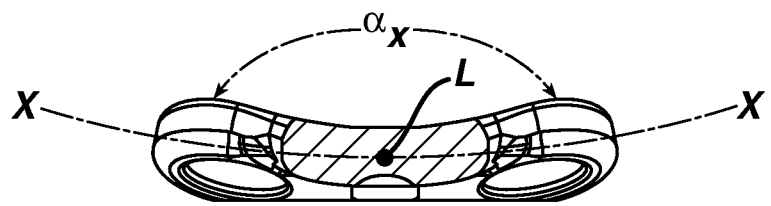
FIG. 2B is a cross-sectional view of the fixation plate shown in FIG. 1A taken along line B-B.
Figure 2C:
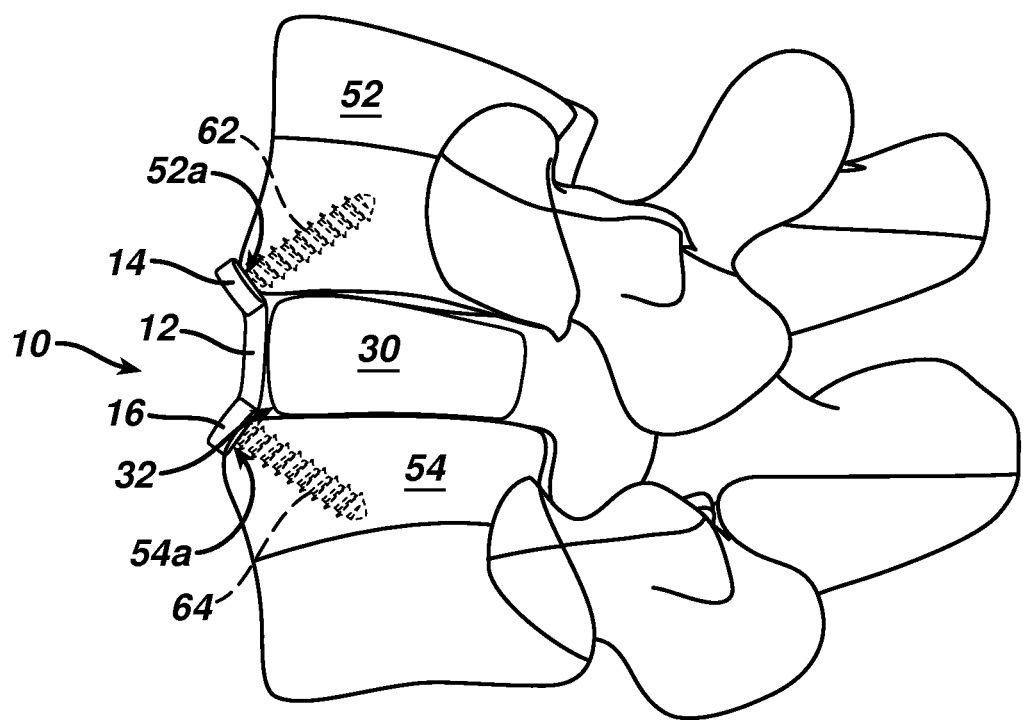
FIG. 2C is a side view of a portion of a human spine having the fixation plate shown in FIG. 1A implanted therein.

The plate 10 can also include or alternatively have a curve X, as best shown in FIGS. 1B, 1C, and 2B, that is formed about the longitudinal axis L in a sagittal plane, which extends in a superior-inferior direction and dissects the posterior and anterior faces 12a, 12b, 14a, 14b, 16a, 16c of the plate 10. The curve X is preferably only formed about the longitudinal axis L that extends between the superior and inferior portions 14, 16. More particularly, the plate 10 can be curved such that the opposed edges 12c, 12d of the mid-portion 12 are substantially longitudinally straight, but they are positioned posterior to the posterior face 12b of the mid-portion 12. As a result of the curve X, the posterior face 12b, 14b, 16b of each portion 12, 14, 16 can have a substantially concave shape about the longitudinal axis L. The anterior face 12a, 14a, 16a of each portion 12, 14, 16 can also optionally have a substantially convex shape about the longitudinal axis L to correspond to the posterior face 12b, 14b, 16b.

The curve X can also continue through the superior and inferior portions 14, 16 of the plate 10, such that the opposed edges 14c, 14d, 16c, 16d of the superior and inferiors portions 14, 16 are positioned posterior to the posterior faces 14b, 16b thereof. As previously discussed, the superior and inferior portions 14, 16 can also be angled in a direction anterior to the anterior faces 14a, 16a thereof. When the angle $\alpha_T$ and the curve X are combined, the opposed thru-bore tabs 15a, 15b, 17a, 17b are not only angled anterior to the anterior face 12a of the mid-portion 12 of the plate 10, but they are also angled toward one another in a posterior direction. While the angle $\alpha_x$, shown in FIGS. 1C and 2B, can vary, in an exemplary embodiment the angle $\alpha_x$ between the thru-bore tabs 15a, 15b, 17a, 17b is in the range of about 150° to 180°, and more preferably the angle is about 160°. A person skilled in the art will appreciate that where the angle $\alpha_x$ is 180°, the plate 10 will not have a curve X formed therein, but rather it will be substantially planar.

In use, the plate 10 can be implanted in the lumbar, cervical, or thoracic regions of the patient's spine, and thus the size of the plate 10 will vary depending on the intended use. The plate 10 can also be adapted for use in various surgical approaches, but preferably the plate 10 is adapted for anterior fixation. In an exemplary embodiment, the plate 10 has a length/and/or width w that is adapted for use in the lumbar region of a patient's spine. More preferably, the plate 10 has a length l that is less than a distance between the adjacent vertebrae to which the plate 10 is adapted to be mated to. This allows the superior and inferior portions 14, 16 of the plate 10, and in particular the thru-bore tabs 15a, 15b, 17a, 17b, to be positioned on the anterior rims of the adjacent vertebrae, as previously discussed above. A person skilled in the art will appreciate that the plate 10 can be adapted for a variety of other uses and the configuration of the plate 10 can vary depending on the intended use. Moreover, a variety of plates 10 having various sizes and configurations can be provided as part of a kit, allowing a surgeon to select the appropriate plate 10 based on the intended use.

By way of non-limiting example, FIG. 2C illustrates plate 10 implanted in a patient's spinal column. In particular, the plate 10 is shown mated to adjacent vertebrae 50, 52 having an implant, e.g., fusion cage 30, disposed therebetween. The adjacent vertebrae 52, 54 are distracted, at least a portion of the disc is removed, and the area is prepared using techniques known in the art. Prior to inserting the fusion cage 30 between the adjacent vertebrae 52, 54, the fusion cage 30 can be filled with autograft, allograft bone, and/or demineralized bone matrix to promote fusion. The fusion cage 30 is then positioned between the vertebrae 52, 54 using a variety of devices. Distractor and spreader devices are known in the art, and are effective for separating adjacent vertebrae, and optionally assisting with insertion of the implant. Typical distractors include two opposed blade members which are inserted between the adjacent vertebrae, and then opened to separate the vertebrae. The fusion cage 30 can then be inserted into the disc space either manually, or using an impacting device, such as a mallet.

Once the fusion cage is in position, the fixation plate 10, and in particular the posterior surface 12*b* of the plate 10, can be placed adjacent to the anterior face 32 of the fusion cage 30 to position the superior and inferior portions 14, 16 of the plate 10 against the anterior rims 52*a*, 54*a* of the adjacent vertebrae 52, 54. Once positioned against the vertebrae, the plate 10 is preferably not fixedly attached to the fusion cage 30 such that the two components are in a non-mating relationship with one another. In other words, the plate 10 and the fusion cage 30 remain as separate components from one another. One or more bone screws (only two screws 62*a*, 64 are shown) can then be inserted through the thru-bores 20*a*, 20*b*, 22*a*, 22*b* in the superior and inferior portions 14, 16 of the plate 10 to secure the plate 10 to the adjacent vertebrae 52, 54. A person skilled in the art will appreciate that various procedures and tools can be used to position the plate 10 against the adjacent vertebrae and to prepare the vertebrae for receiving the bone screws. The plate 10 can also optionally include various features to allow the plate 10 to be coupled to a tool for implanting the plate 10.

Figure 3A:
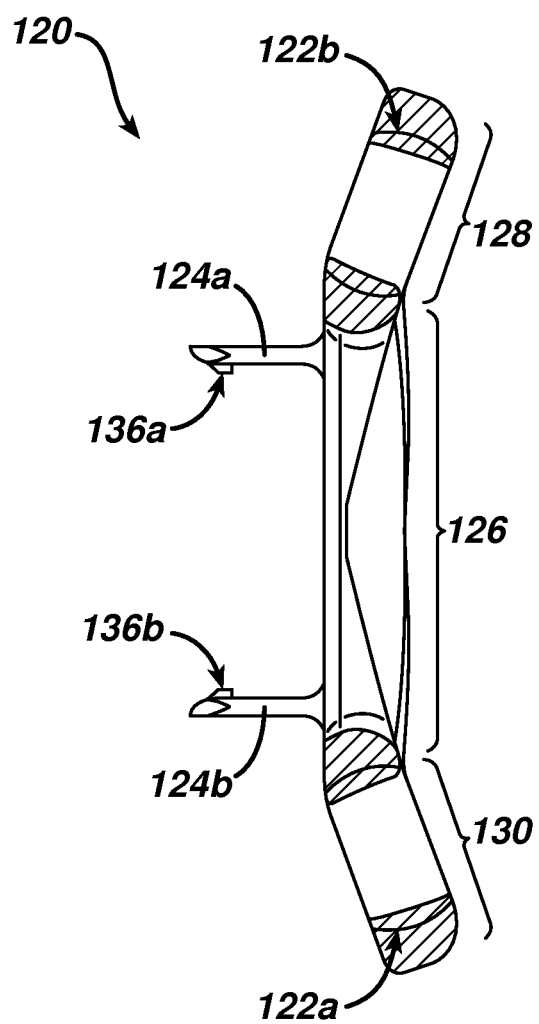
FIG. 3A is side view of an embodiment of a spinal fixation plate that is adapted to mate to a fusion cage.
Figure 3B:
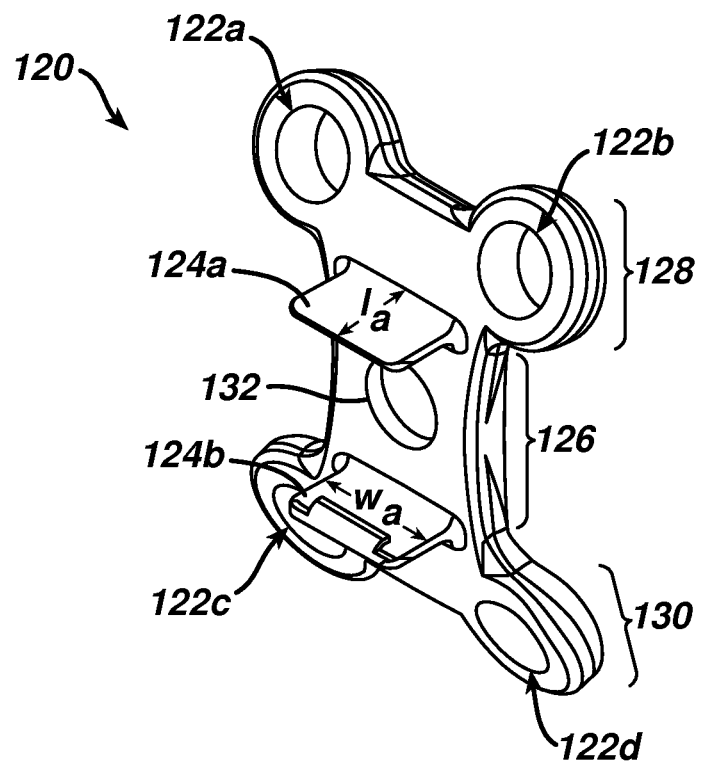
FIG. 3B is a posterior perspective view of the plate shown in FIG. 3A.
Figure 4A:
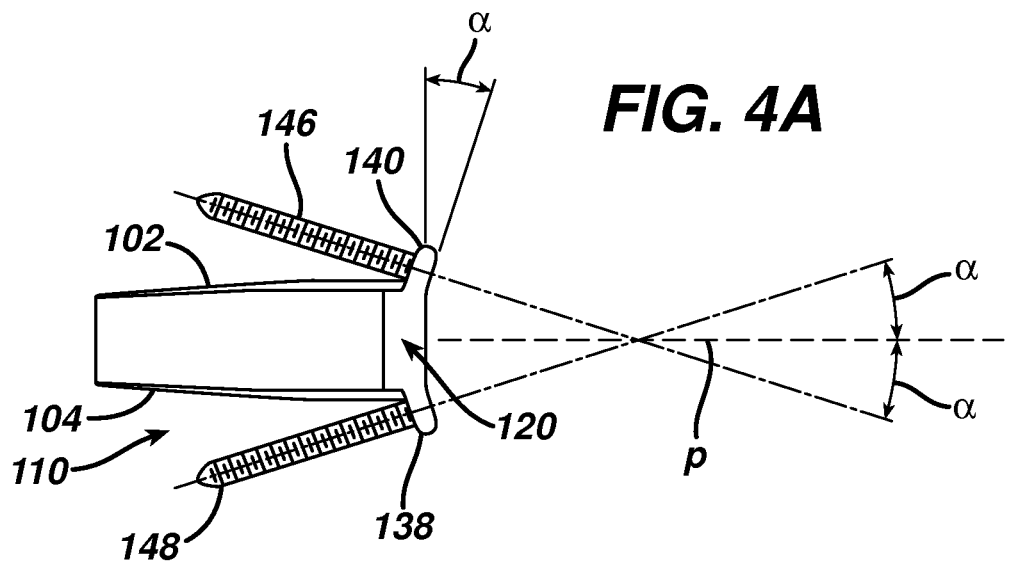
FIG. 4A is a side view of the plate shown in FIGS. 3A and 3B mated to one embodiment of a fusion cage to form a spinal fixation assembly.

FIGS. 3A-3B illustrate another embodiment of a spinal fixation plate 120. In this embodiment, the plate 120 is adapted to mate to a vertebral implant, such as a fusion cage 110, shown in FIGS. 4A-4B. FIG. 4A illustrates plate/cage assembly 100. The plate 120 can have a generally planar shape and it includes a mid-portion 126 that is positioned between superior and inferior portions 128, 130. When the plate 120 is mated to the fusion cage 110, the superior portion 128 of the plate 120 is adapted to extend beyond a superior surface 102 of the fusion cage 110, and the inferior portion 130 of the plate 120 is adapted to extend beyond an inferior surface 104 of the fusion cage 110. While the plate 120 is preferably substantially planar, the mid-portion 126 of the plate 120 can be curved to contour the shape of an anterior face 108 of the fusion cage 110.

Figure 4B:
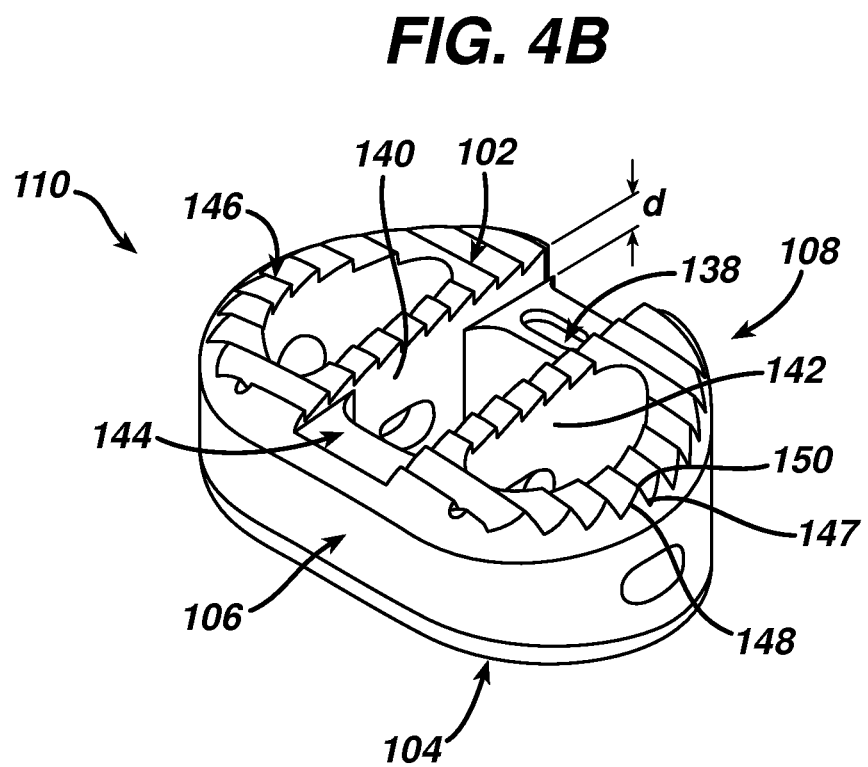
FIG. 4B is a perspective view of the fusion cage shown in FIG. 4A.

Each of the superior and inferior portions 128, 130 of the plate 120 further include at least one aperture 122*a-d* formed therein for receiving a bone screw to secure the plate 120 to a vertebra. As shown, the superior and inferior portions 128, 130 of the plate 120 each include two apertures 122*a*, 122*b*, 122*c*, 122*d* formed therein. The apertures 122*a-d* can have a variety of configurations, and exemplary configurations will be discussed in more detail with respect to FIGS. 6-10. FIGS. 4A-4B illustrate plate 120 mated to implant 110, and apertures 122*a-d* having bone screws 146 and 148 disposed therethrough, each having a head and a shank.

The superior and inferior portions 128, 130 of the plate 120 can also extend at an angle with respect to the mid-portion 126 of the plate 120. In particular, referring to FIG. 4A, which shows plate 120 mated to cage 110, superior and inferior portions 128, 130 are angled with respect to the remainder of the plate 120 so that screws 146 and 148 extending therethrough are angled with respect to a medial plane "P" of the body 110. The angle formed by the tab(s) and plate, as well as by the screw(s) and medial plane, is designated as "a" and it can vary depending on a patient's particular anatomy. Although the angle α can range from 15° to 60°, for most applications the angle α is about 20°. However, in other embodiments, the superior and inferior portions 128, 130 can be flexible or readily bent with respect to the remainder of the plate 120.

The mid-portion 126 of the plate 120 can also include a central aperture 132 formed therein. The central aperture 132 is positioned such that it is aligned with a central bore (not shown) formed in the fusion cage 110 when the plate 120 is mated to the cage 110. The central aperture 132 and bore can be effective to receive an insertion tool and/or a fastening element, such as a screw, effective to mate the plate 120 to the fusion cage 110. In one embodiment (not shown), the fastening element can be fixedly, but rotatably disposed within the central aperture 132 of the plate 120, and/or it can be adapted to snap into the central bore in the fusion cage 110. The fastening element can further be adapted to engage the fusion cage 110 upon rotation thereof. A person having ordinary skill in the art will appreciate that a variety of techniques can be used to mate the plate 120 to the fusion cage 110.

Still referring to FIGS. 3A-4B, the plate 120 can also include a mating element 124*a*, 124*b* that is adapted to slidably engage and mate the plate 120 to the anterior face 108 of the fusion cage 110 in an anterior-posterior direction. While the mating element 124*a*, 124*b* can have a variety of configurations, FIGS. 3A-3B illustrate first and second opposed arms 124*a*, 124*b* that extend outward from the plate 120 in a direction substantially perpendicular to the substantially planar surface of the plate 120. The arms 124*a*, 124*b* can be positioned anywhere on the plate 120, but preferably the first arm 124*a* is positioned just superior to the mid-portion 126 of the plate 120 between the central aperture 132 and the superior apertures 122*a*, 122*b* formed in the superior portion 128 of the plate 120, and the second arm 124*b* is positioned just distal to the mid-portion 126 of the plate 120 between the central aperture 132 and the inferior apertures 122*c*, 122*d* formed in the inferior portion 130 of the plate 120. In other words, the arms 124*a*, 124*b* are positioned such that, when the plate 120 is mated to the fusion cage 110, the arms 124*a*, 124*b* are configured to engage the superior and inferior faces 102, 104 of the fusion cage 110.

The shape of the arms 124*a*, 124*b* can also vary, but preferably each arm 124*a*, 124*b* is adapted to contour the shape of the fusion cage 110. By way of non-limiting example, where the fusion cage 110 has domed or convex superior and inferior surfaces 102, 104, the arms 124*a*, 124*b* are preferably convex to contour the shape of the fusion cage 110. The size of each arm 124*a*, 124*b* can vary as well, but preferably each arm 124*a*, 124*b* has a length $l_a$ sufficient to enable the arms 124*a*, 124*b* to extend across at least a portion of the superior and inferior surfaces 102, 104 of the fusion cage 110, and a width $w_a$ sufficient to allow the arms 124*a*, 124*b* to grasp the fusion cage 110.

Each arm 124*a*, 124*b* can have a variety of configurations, but preferably the arms 124*a*, 124*b* include an engagement element 136*a*, 136*b* effective to engage the superior and inferior faces 102, 104 of the fusion cage 110. The engagement element 136*a*, 136*b* preferably provides an interference fit to temporarily secure the plate 120 to the fusion cage 110. While the engagement element 136*a*, 136*b* can have a variety of configurations, the engagement element 136*a*, 136*b* can be, for example, in the form of at least one protrusion formed on an inner surface of each arm 124*a*, 124*b* that is adapted to sit in at least one indentation 138 (shown in FIG. 4B) formed in each of the superior and inferior faces 102, 104 of the fusion cage 110. As shown in FIG. 3A, the protrusion 136*a*, 136*b* on each arm 124*a*, 124*b* has a generally elongate shape. The indentation will be discussed in more detail with respect to FIG. 4B below. The arms 124a, 124b can optionally be flexible to allow the arms 124a, 124b to flex outward while sliding the plate 120 onto the fusion cage 110, and to allow the arms 124a, 124b to then return to their original state whereby the protrusions 136a, 136b on the arms 124a, 124b to snap into the indentations 138 (only one indentation is shown in FIG. 4B) formed in the superior and inferior faces 102, 104 of the fusion cage 110.

Referring now to FIG. 4B, fusion cage 110 is shown in more detail. The fusion cage 110 can have a variety of configurations, but as previously stated it generally includes superior 102, inferior 104, posterior 106, and anterior 108 faces. The inferior and superior faces 102, 104 can have a flat to slightly convex shape, and/or a slightly tapered (about 10°) or wedge profile, wherein the body 110 is thicker at the anterior face 108 than at the posterior face 106.

A central bore (not shown) can be formed in the anterior face 102 of the fusion cage 110, and it preferably includes threads formed therein for receiving a fastening element, e.g., a screw. The threads are preferably spinal lock threads to provide a secure connection between the plate and the cage. First and second transverse elements 140, 142 can join the posterior face 106 to the anterior face 108, and a guide path 144 for receiving an insertion tool can extend across the superior and inferior faces 102, 104 between the posterior and anterior faces 106, 108.

Fusion cage 110 further includes an arm-seating recess formed in each of the superior and inferior surfaces 102, 104 for receiving the arms 124a, 124b formed on the plate 120. The recesses can be formed in the guide path 144, or more preferably the guide path 144 can form arm-seating recesses, as is shown in FIG. 4B. Each guide path 144 (only the guide path on the superior surface 102 is shown), or arm-seating recess, preferably has a depth d sufficient to receive the corresponding arm 124a, 124b formed on the plate 120 such that, when the plate 120 is mated to the fusion cage 110, the arms 124a, 124b are flush with the superior and inferior surfaces 102, 104 of the fusion cage 110. This is particularly advantageous in that it allows the fusion cage 110 to be positioned between adjacent vertebrae prior to inserting the arms 124a, 124b into the arm-seating recesses 144 to attach the plate 120 to the fusion cage 110. Each of the arm-seating recesses 144 further preferably includes at least one indentation 138 formed therein for receiving the protrusion 136a, 136b formed on the inner surface of each arm 124a, 124b. As shown, the indentation 138 is in the form of an elongate groove that is adapted to receive and seat the protrusion 136a, 136b formed on each arm 124a, 124b. A person having ordinary skill in the art will appreciate that the arms 124a, 124b can merely slide into and seat within the recess 144 formed in the fusion cage 110, and that they do not need to engage the fusion cage 110. An engagement mechanism is merely preferred to allow the plate 120 to be at least temporarily secured to the fusion cage 110 during implantation.

The fusion cage 110 can optionally include a number of bone engaging surface features 146 formed on the superior and inferior surfaces 102, 104 to facilitate the secure mounting of the cage 110 between adjacent vertebrae. The bone engaging surface features 146 can be present on the entire surface area of the superior and inferior surfaces 102, 104, or optionally, selected regions of the superior and inferior surfaces 102, 104 can be free of surfaces features 146. The bone engaging surface features 146 can have a variety of shapes, but are preferably in the form of wedge-shaped ridges that extend is a direction transverse to the posterior 106 and anterior 108 faces of the fusion cage 110. Each bone engaging surface feature 146 includes a posterior side wall 148 and an anterior side wall 149, which meet at a peak 150. The side walls 148, 149 of each surface feature 146 can be angled or sloped to facilitate insertion of the cage 110 between adjacent vertebrae and to assist in preventing the fusion cage 110 from becoming dislodged. The size of the surface features 146 can also vary but preferably the surface features 146 have a size sufficient to cause each surface feature 146 to engage and penetrate the adjacent vertebrae. It will be understood that while ridges 146 have been shown in a preferred embodiment, it is contemplated that there are a variety of structures which could provide a surface for effective engagement with the vertebral bodies to limit expulsion from the disc space.

Figure 5:
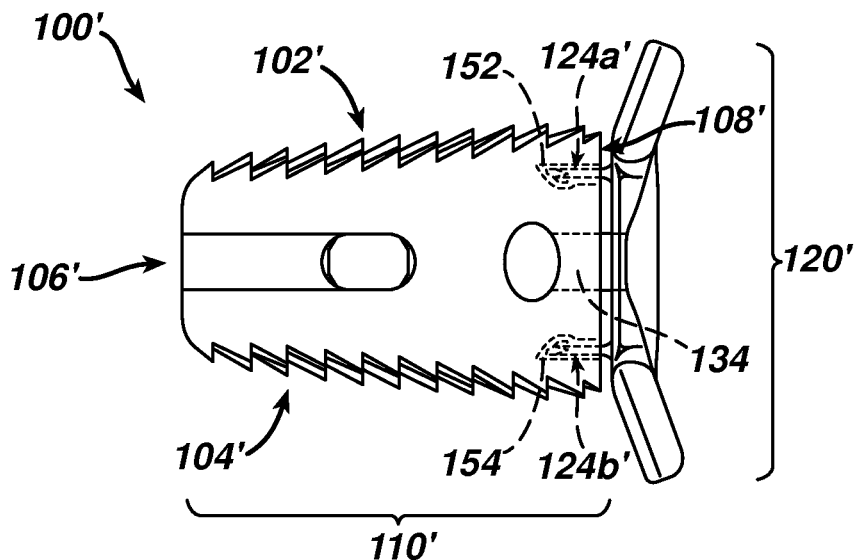
FIG. 5 is a side view of another embodiment of a spinal fixation assembly.

FIG. 5 illustrates another embodiment of a spinal fixation assembly 100'. In this embodiment, the arms 124a, 124b on the plate 120 are adapted to extend into opposed superior and inferior bores 152, 154, rather than recesses 144, formed in the fusion cage 110'. As shown, the arms 124a, 124b can merely slide into the bores 152, 154 that extend into the fusion cage 110' to provide an alignment mechanism between the cage 110' and the plate 120. The bores 152, 154 can optionally be adapted to receive the engagement mechanism 136a, 136b formed on each arm 124a, 124b to at least temporarily secure the arms 124a, 124b within the bores 152, 154. By way of non-limiting example, the arms 124a, 124b and the bores 152, 154 can each be tapered to provide an interference fit between the arms 124a, 124b and the bores 152, 154. Alternatively, the arms 124a, 124b can include a press-fit pin that depresses upon insertion of the arms 124a, 124b into the bores 152, 154, and then once each arm 124a, 124b is fully inserted into the bore 152, 154, returns to its originally state whereby the pins extending into corresponding indentations formed within the bores 152, 154. A person having ordinary skill in the art will appreciate that a variety of mechanisms can be used to secure the arms 124a, 124b of the plate 120 within the bores 152, 154 formed in the fusion cage 110'.

In use, the adjacent vertebrae are prepared and distracted and the fusion cage 110 is placed therebetween, as previously described above. Once the fusion cage 110 is in position, the fixation plate 120 can be placed adjacent to the anterior face 108 of the fusion cage 110 to position the superior and inferior portions 128, 130 of the plate 110 against the anterior rims of the adjacent vertebrae. The plate 120 is then preferably mated to the anterior face 108 of the fusion cage 110 by positioning the arms 124a, 124b between the superior and inferior surfaces 102, 104 of the fusion cage 110 and the adjacent vertebrae. Where plate 120' is used and the cage 110' includes arm-receiving recesses 152, 154, the arms 124a', 124b' of the plate 120' can be easily slid into the recesses 152, 154 to engage the cage 110'. A center screw (not shown) can then be inserted through a central aperture 132 in the plate 120 and through a bore in the cage (e.g., FIG. 5 shows bore 134 formed in the cage 110') to secure the plate 120 to the cage 110, and one or more bone screws (only two bone screws 146, 148 are shown in FIG. 4A) can be inserted through the apertures 122a, 122b, 122c, 122d in the superior and inferior portions 128, 130 of the plate 120 to secure the plate 120 to the adjacent vertebrae.

The present invention also provides a variety of configurations for securing a spinal fixation plate to adjacent vertebrae. In particular, FIGS. 6-10 illustrate embodiments of different apertures for use with a plate according to the present invention. The apertures are adapted to provide a more secure connection between the plate and a vertebrae. While the various embodiments will be described in relation to particular spinal fixation plates disclosed herein, a person having ordinary skill in the art will appreciate that the virtually any technique known in the art can be used with any of the various embodiments of spinal fixation plates, as well as with a variety of vertebral implants.

Figure 6:
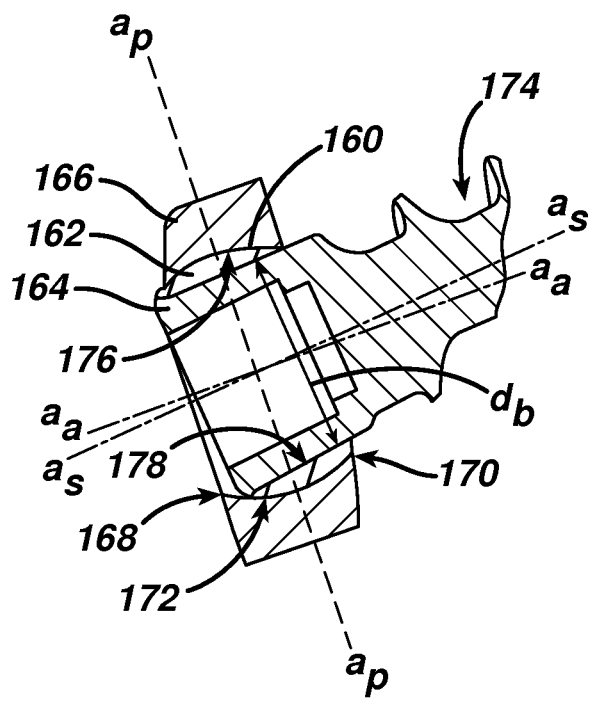
FIG. 6 is a cut-away view of an aperture, split bushing, and bone screw according to another embodiment of the present invention.

FIG. 6 illustrates one embodiment of an aperture 160 formed in a tab 166 of a plate and having a split bushing 162 disposed therein. A bone screw 174 is disposed through the aperture 160 and the split bushing 162. The aperture 160 includes a first end 168, a second end 170, and a sidewall 172 extending therebetween. The first end 168 is preferably adapted to receive a bone screw 174, or similar type of fixation element, and to seat the head 164 of the bone screw 174 therein. The aperture 160 can extend through the tab 166 in the plate along a central axis $\alpha_a$ that is substantially perpendicular to a central plane $\alpha_p$ of the tab 166, or alternatively the central axis $a_a$ of the aperture 160 can be offset from, or disposed at an angle with respect to, the plane $a_p$ of the tab 166. The sidewall 172 of the aperture 160 can also vary and can be either substantially planar along the length thereof between the first and second ends 168, 170 of the aperture 160, or the sidewall 172 can be curved or can extend at an angle. As shown in FIG. 6, the sidewall 172 has a substantially concave shape to receive the split bushing 162.

The split bushing 162 is disposed within the aperture 160 and it has a generally cylindrical shape with a gap (not shown) formed therein to allow the bushing 162 to be expanded. The split bushing 162 includes an outer surface 176 which can have a shape adapted to conform to the shape of the sidewall 172 of the aperture 160, and an inner surface 178 which is adapted to receive a bone screw 174. By way of non-limiting example, the split bushing 160 can have a convex outer surface 172 to allow the split bushing 162 to sit within the concave sidewall 172 of the aperture 160. The split bushing 162 further includes an inner diameter $d_b$ that can vary between opposed first and second ends 168, 170 of the split bushing 162. Preferably, the diameter $d_b$ of the bushing 162 at the first end 168 is larger than the diameter $d_b$ of the bushing 162 at the second end 170. The tapered diameter allows the bushing 162 to receive a portion of the tapered undersurface of the head 164 of the bone screw 174.

Figure 7:
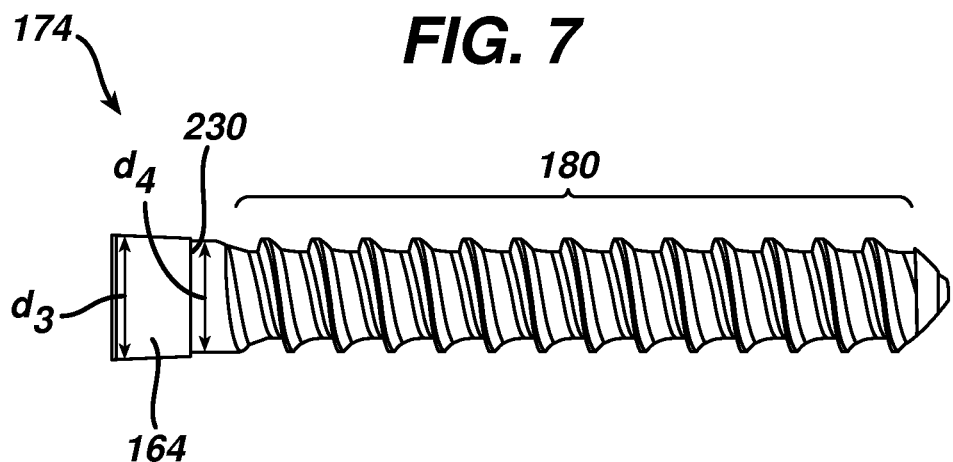
FIG. 7 is a side view of one embodiment of a bone screw according to the present invention.

FIG. 7 illustrates the bone screw 174 in more detail having a tapered head 164 adapted to fit within the split bushing 162 shown in FIG. 6. As shown, the bone screw 174 includes a head 164 and a threaded shank 180. The head 164 is tapered preferably at an angle substantially the same as the angle of the tapered inner diameter $d_b$ of the split bushing 162. In use, upon tightening the bone screw 174, the split bushing 162 expands and provides an interference fit between the bone screw 174 and the aperture 160, thereby creating a rigid lock to secure the plate to a vertebrae. The tapered diameter $d_b$ of the bushing 162 also allows the bone screw 174 to be inserted at variable angles $a_s$ with respect to the central axis $a_a$ of the aperture, as shown in FIG. 6.

Figure 8:
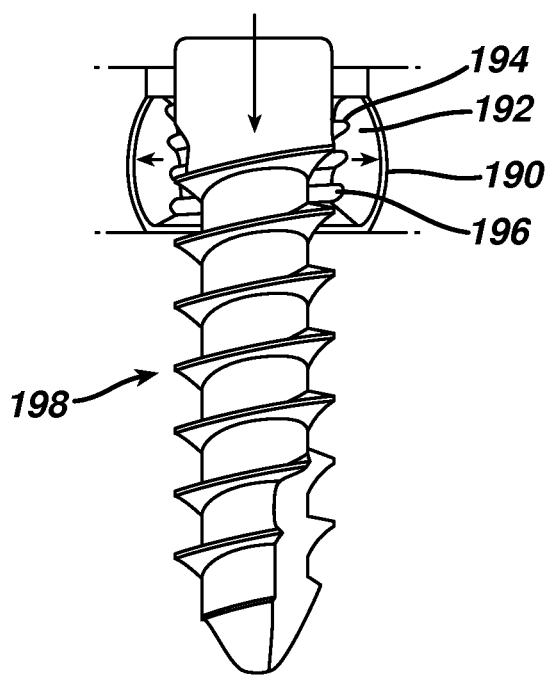
FIG. 8 is a cut-away view of another embodiment of an aperture, split bushing, and bone screw according to the present invention.

FIG. 8 illustrates another embodiment of an aperture 190 having a split bushing 192 disposed therein. In this embodiment, the split bushing 192 includes threads 194 formed on an inner surface thereof to mate with corresponding threads 196 formed on a bone screw 198. The threads 194, 196 are particularly effective to prevent the bone screw 198 from backing out of the aperture 190, and to provide a rigid lock between the screw 198 and the aperture 190 thereby securely mating the plate to a vertebrae. In this embodiment, the aperture 190 preferably includes an anti-rotation mechanism effective to prevent the split bushing 192 from rotating while the screw 198 is threaded therethrough. The anti-rotation mechanism can have a variety of configurations and, by way of non-limiting example, can be a pin or raised protrusion (not shown) disposed within the aperture 190 and adapted to extend into the gap formed in the split bushing 192.

Figure 9:
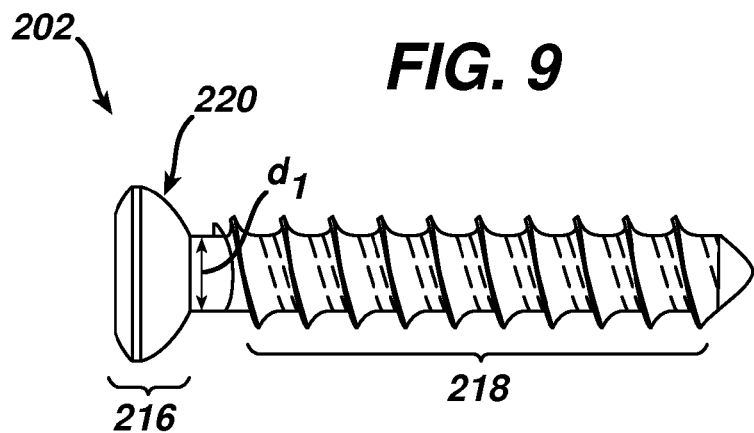
FIG. 9 is a side view of another embodiment of a bone screw according to the present invention.
Figure 10:
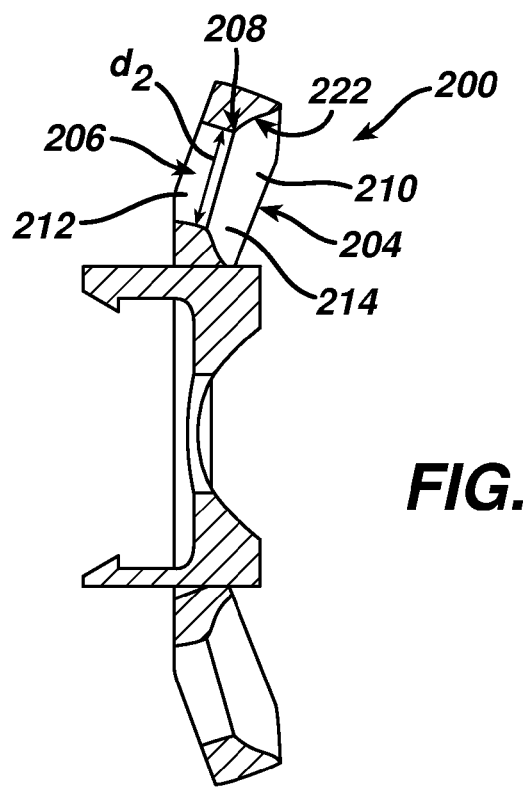
FIG. 10 is a cut-away, side view of a plate having apertures adapted to receive the bone screw shown in FIG. 9.

FIGS. 9-10 illustrate yet another embodiment of an aperture 200 and bone screw 202 for use with the present invention. As shown in FIG. 10, the aperture 200 includes a first end 204, a second end 206, and a sidewall 208 extending therebetween and defining an inner lumen 210. The inner lumen 210 includes a first portion 214 positioned adjacent the first end 204, and a second portion 212 positioned adjacent the second end 206 of the aperture 200. The first portion 214 of the inner lumen 210 has a shape and size adapted to receive the head 216 of a bone screw 202. FIG. 9 illustrates an exemplary embodiment of a bone screw 202 for use with a plate having an aperture 200 as shown in FIG. 10. The bone screw 202 includes a head 216 and a threaded shank 218. The head 216 of the bone screw 202 includes a substantially convex, slightly rounded outer surface 220. The first portion 214 of the inner lumen 210 of the aperture 200 has a concave sidewall 222, e.g., a generally spherical recess, to allow the rounded head 216 of the bone screw 202 to seat therein. The second portion 212 of the inner lumen 210 is substantially cylindrical and has a shape and size adapted to receive the threaded shank 218 of a bone screw 202. Preferably, the second portion 212 of the inner lumen 210 has a diameter $d_2$ greater than a diameter $d_1$ of the shank 218 of the bone screw 202. In use, the first and second portions 214, 212 of the inner lumen 210 allow the bone screw 202 to translate within the aperture 200 such that the screw 202 can be inserted at varying angles. While the aperture 200 does not include a split bushing to provide a rigid connection between the bone screw 202 and the plate, the aperture 200 allows the full exertion of natural biomechanical compression stresses through the vertebral bodies into which the screw 202 is inserted.

Referring back to FIG. 7, in yet another embodiment, the bone screw 174 can include a shoulder 230 formed thereon that abuts a corresponding shoulder (not shown) formed in an aperture. The shoulder 230 is formed by a difference, or stepped increase, in the diameter $d_3$, $d_4$ of the screw head 164 and in the diameter of the aperture, or in the split bushing if the aperture includes one. In use, the bone screw 174 is inserted through an aperture and once the shoulder 230 on the screw head 164 passes the shoulder 230 in the aperture, or in the split bushing, the shoulders will engage thereby preventing the screw 174 from backing out of the aperture.

The fusion cage and plate of the present invention can be made from a variety of materials. By way of non-limiting example, a carbon fiber composite or other radiolucent material is well suited for fabrication of the body, and titanium or carbon fiber composites are suitable materials for the plate 20.

As should be readily apparent from the preceding description, the present invention provides many advantages. For example, the fusion cage can be sufficiently broad and thick so that only a single cage is needed to replace an excised disc. The profile and slightly bowed or convex superior and inferior surfaces of the fusion cage body closely approximate the shape of a natural disc and provide an excellent, stable, load-bearing surface. The plate, when included, ensures that the body will not become dislodged from the spine, yet is readily accessible with an anterior approach. Further, the plate allows bone screws to be deeply embedded into the vertebral bodies without piercing or otherwise damaging the hard, load-bearing, cortical bone. Also, both the plate and the body include features that allow for relatively easy manipulation and insertion with appropriately configured surgical tools.

Of course, one skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for implanting a spinal fixation plate, comprising:
   positioning a spinal fixation plate having a mid-portion, a superior portion, and an inferior portion to extend between adjacent superior and inferior vertebrae;
   inserting at least one fastening element through at least one thru-bore formed in the superior portion of the spinal fixation plate and through an anterior rim of the superior vertebra;
   inserting at least one fastening element through at least one thru-bore formed in the inferior portion of the spinal fixation plate and through an anterior rim of the inferior vertebra;
   wherein a length of the spinal fixation plate in a superior to inferior direction is greater than a maximum width of the spinal fixation plate, and the superior and inferior portions are positioned at an angle with respect to the mid-portion of the plate in a direction anterior to an anterior face of the mid-portion such that the mid-portion is flush or sub-flush relative to anterior faces of the inferior and superior vertebrae.

2. The method of claim 1, further comprising, prior to the step of positioning a spinal fixation plate, distracting the adjacent vertebrae and removing at least a portion of a vertebral disc disposed therebetween.

3. The method of claim 2, further comprising, after the steps of distracting and removing, inserting a spinal implant between the adjacent vertebra.

4. The method of claim 3, wherein the mid-portion of the spinal fixation plate is positioned adjacent an anterior face of the implant.

5. The method of claim 3, wherein the spinal implant comprises an inner body fusion device.

6. The method of claim 3, wherein the spinal implant comprises an artificial disc.

7. The method of claim 1, wherein the superior and inferior portions of the spinal fixation plate include longitudinally opposed thru-bore tabs, each having the at least one thru-bore formed therein for receiving the at least one fastening element.

8. The method of claim 7, wherein the opposed thru-bore tabs in the superior portion are angled toward one another in a posterior direction, and the thru-bore tabs in the inferior portion are angled toward one another in the posterior direction.

9. The method of claim 7, wherein an angle between a posterior face of a first thru-bore tab and a posterior face of a second thru-bore tab in each of the superior and inferior portions is in the range of about 150° to 180°.

10. The method of claim 7, wherein an angle between a posterior face of a first thru-bore tab and a posterior face of a second thru-bore tab in each of the superior and inferior portions is about 160°.

11. The method of claim 1, wherein an angle between an anterior face of the superior and inferior portions and an anterior face of the mid-portion is less than about 15°.

12. A method for implanting a spinal fixation plate, comprising:
    positioning a spinal fixation plate to extend between adjacent superior and inferior vertebrae, the spinal fixation plate having a mid-potion, a superior portion, and an inferior portion;
    inserting at least one fastening element through at least one thru-bore tab formed in the superior portion of the spinal fixation plate and through an edge of an anterior rim of the superior vertebra; and
    inserting at least one fastening element through at least one thru-bore tab formed in the inferior portion of the spinal fixation plate and through an edge of an anterior rim of the inferior vertebral;
    wherein the at least one thru-bore tab in the superior portion has an anterior face positioned anterior to an anterior face of the mid-portion and the at least one thru-bore tab in the inferior portion has an anterior face positioned anterior to the anterior face of the mid-portion, and the plate has a posterior curvature formed about a longitudinal axis extending between the superior and inferior portions such that each of the at least one fastening elements are inserted through the anterior rims of the vertebrae.

13. The method of claim 12, wherein a length of the spinal fixation plate is less than a distance between the superior and inferior vertebrae such that the mid-portion of the plate is flush or sub-flush relative to anterior faces of the vertebrae.

14. The method of claim 12, wherein an angle between the anterior face of the superior and inferior portions and the anterior face of the mid-portion is less than about 15°.

15. The method of claim 12, further comprising, prior to the step of positioning a spinal fixation plate, distracting the adjacent vertebrae and removing at least a portion of a vertebral disc disposed therebetween.

16. The method of claim 12, further comprising inserting a spinal implant between the vertebrae prior to positioning the spinal fixation plate to extend between the vertebrae, the spinal fixation plate being in a non-mating relationship with the spinal implant.

* * * * *